(12) United States Patent
Moon et al.

(10) Patent No.: US 6,710,215 B2
(45) Date of Patent: Mar. 23, 2004

(54) METHOD OF A SIMULTANEOUS PREPARATION OF HEXAFLUOROPROPYLENE AND OCTAFLUOROCYCLOBUTANE

(75) Inventors: Dong Ju Moon, Seoul (KR); Moon Jo Chung, Seoul (KR); Young Soo Kwon, Seoul (KR); Byoung Sung Ahn, Seoul (KR)

(73) Assignee: Korea Institute of Science and Technology, Seoul (KR)

( * ) Notice: Subject to any disclaimer, the term of this patent is extended or adjusted under 35 U.S.C. 154(b) by 103 days.

(21) Appl. No.: 10/218,362

(22) Filed: Aug. 14, 2002

(65) Prior Publication Data

US 2004/0034259 A1 Feb. 19, 2004

(51) Int. Cl.$^7$ .................. C07C 17/00; C07C 17/02; C07C 17/04; C07C 21/18; C07C 21/20; C07C 21/22; C07C 19/08; C07C 23/00; C07C 25/13

(52) U.S. Cl. .................. 570/153; 570/123; 570/138; 570/149

(58) Field of Search ................... 570/138, 149, 570/153, 123, 124

(56) References Cited

U.S. PATENT DOCUMENTS

| 2,384,821 A | 9/1945 | Downing et al. |
| 2,394,581 A | 2/1946 | Benning et al. |
| 2,404,374 A | 7/1946 | Harmon |
| 2,759,983 A | 8/1956 | Waddell |
| 3,009,966 A | 11/1961 | Hauptschein et al. |
| 3,446,858 A | 5/1969 | Shingu et al. |
| 4,849,554 A | 7/1989 | Cresswell et al. |

FOREIGN PATENT DOCUMENTS

| EP | 0 445 399 | 9/1991 |
| EP | 0 451 793 | 10/1991 |
| EP | 0 287 219 | 5/1992 |
| JP | 57-59822 | 4/1982 |

*Primary Examiner*—Samuel Barts
*Assistant Examiner*—Elvis O. Price
(74) *Attorney, Agent, or Firm*—Scully, Scott, Murphy & Presser

(57) ABSTRACT

A method of simultaneous and selective prepararation of hexafluoropropylene and octafluorocyclebutane comprising the steps of:

(a) thermally decomposing difluorochloromethane to obtain tetrafluoroethylene and then supplying the resulting tetrafluoroethylene into a fluidized bed reactor equipped with a distributor for supplying steam; and (b) supplying steam into a flow of tetrafluoroethylene supplied into the fluidized bed reactor, through a distributor for supplying steam at a certain molar ratio of tetrafluoroethylene/stream, and then performing dimerization of tetrafluoroethylene in the fluidized bed reactor under an atmospheric pressure.

5 Claims, 1 Drawing Sheet

METHOD OF A SIMULTANEOUS PREPARATION OF HEXAFLUOROPROPYLENE AND OCTAFLUOROCYCLOBUTANE

BACKGROUND OF THE INVENTION

1. Field of the Invention

The present invention relates to a method of a simultaneous preparation of hexafluoropropylene (hereinafter, referred to as 'HFP') and octafluorocyclobutane (hereinafter, referred to as 'RC318').

2. Description of the Background Art

In general, HFP is a monomer used as a raw material for a fluoride group resin copolymer, and a principal raw material for a fluoride resin together with tetrafluoroethylene (hereinafter, referred to as 'TFE').

As preparation methods of HFP, a simultaneous preparation of TFE and HFP through a thermal decomposition of difluorochloromethane (hereinafter, referred to as 'R22') (EP No. 0 287 219 and U.S. Pat. No. 4,849,554), a thermal decomposition of TFE and RC318 (U.S. Pat. No. 3,446,858), a thermal decomposition of polytetrafluoroethylene (U.S. Pat. No. 2,759,983) and a thermal decomposition of trifluoromethane (hereinafter, referred to as 'R23') (U.S. Pat. No. 3,009,966) have been reported.

In addition, EP No. 0 287 219 and U.S. Pat. No. 4,849,554 disclose a simultaneous preparation of TFE and HFP through a thermal decomposition of R22 at 750–980° C. for 1–50 milliseconds of a contact time as shown in the below reaction scheme 1.

Reaction Scheme 1

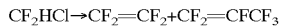

In this method, if the reaction temperature is below 880° C., a conversion of R22 is 40% and a selectivity of HFP is below 9%. If the reaction temperature is 930° C., a conversion of R22 is 50% and a selectivity of HFP is 20%. However, the above preparation method through a thermal decomposition of R22 is not suitable for preparing HFP. It is because there is a difficulty in separation and purification of HFP produced due to its azeotrope formation with R22 which is a starting material, and the selectivity of HFP is low while the selectivity of TFE is high.

In U.S. Pat. No. 2,759,983, Waddell et at. discloses a process for preparing 58% of HFP, 37% of TFE and 2% of RC318 through a thermal decomposition of polytetrafluoroethylene at a reaction temperature of 750–960° C. and a contact time of less than 5 seconds.

RC318 has been used as a propellant, a refrigerant and a cleaner for a semiconductor. As it has been verified with an excellent efficacy as a refrigerant for a turbo compressor of an air-conditioner, it is expected to be a substantially increased demand for it in a freezer market. Recently, Dupont Co. has announced the use of RC318 as a cleaner gas for a semiconductor chemical vapor deposition (CVD) chamber that can replace hexafluoroethane used as a conventional semiconductor cleaner. Due to an influence of hexafluoroethane on global warming, it is anticipated to be highly increased demand for RC318.

As preparation methods of RC318, there have been reported a thermal decomposition of R22 (U.S. Pat. No. 2,384,821), a dimerization of TFE (U.S. Pat. No. 2,404,374, EP No. 0 451 793 and Japanese Patent No. 57-59,822 and Simons electrochemical fluorination using ethylene and TFE as starting materials (European Patent No. 0 445 399) and a thermal decomposition of PTFE (U.S. Pat. Nos. 2,394,581 and 2,759,983) and the like.

Harmon et al. have reported that at least 80% of RC318 is produced when TFE is sufficiently reacted under a superatmospheric pressure at a temperature of 125–500° C. (U.S. Pat. No. 2,404,374). Atkinson and Trenwith have reported that they have conducted a kinetic study related to a thermal decomposition reaction of TFE and a thermal decomposition reaction of RC318, and that when TFE is dimerized at a temperature lower than 600° C., RC318 is mainly produced (J. Chem. Soc., 2082 (1953)). The preparation method of RC318 through the dimerization of TFE at 500° C. is as shown in the following reaction scheme 2.

Reaction Scheme 2

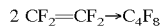

The most general preparation method of RC318 is to dimerize TFE in a tubing reactor. However, because the dimerization of TFE is a severe exothermic reaction, this method has a difficulty in controlling the reaction temperature. In this method, TFE is decomposed into carbon and $CF_4$ at a high temperature, which are accumulated at an outlet of a reactor together with a solid polymer produced and cause a pressure increase in a reaction system. When carbon is accumulated inside the reactor, a reaction pressure is increased, a contact time of TFE is lengthened, and accordingly, the amount of heat generation is increased, so that the reaction proceeds continuously. As a result, the reaction temperature instantaneously rises up above 1000° C., reaching to a situation that the reaction to be stopped. Therefore, the method for preparing RC318 by performing a dimerization of TFE in the tubing reactor is not suitable for being commercialized due to the difficulty in controlling the reaction temperature increase resulting from the severe exothermic reaction.

Hukuseishiro et al. have reported a method for preparing RC318 using TFE and ammonia as starting materials (Japanese Patent No. 57-59,822). In this method, TFE is supplied by bubbling into ammonia, or TFE and ammonia are supplied with respective quantitative pumps into a reactor. The reaction is then carried out at 570–700° C. under a reaction pressure of 0–5 atm with a contact time of 0.3–5 seconds. It has been reported that the conversion is 50–70% and the selectivity of RC318 is 85–86%. However, in this process, if the reaction rate is high, a polymer is produced so as to clog the reaction tube, while if the reaction speed is low, a reaction rate is low. Therefore its industrial utility is low.

A method for preparing RC318 through a thermal decomposition of PTFE has been presented by Benning et al. in 1946 (U.S. Pat. No. 2,394,581). It has been reported that when a thermal decomposition of PTFE is carried out at 575° C., 43% of RC318 is produced.

William Ves et al. disclose a method for preparing RC318 from TFE, ethylene and fluoride (European Patent No. 0 455 399). In this method, ethylene and TFE are reacted in a molar ratio of 10:1 to prepare cyclo-$C_4F_4H_4$ and then Simons electrochemical fluorination is carried out at 40–50° C. to give RC318. This method is as shown in the following reaction schemes 3 and 4, However, this method is unadvisable because the method itself is complicated, costs for devices are high, and corrosion of devices is severe.

Reaction Scheme 3

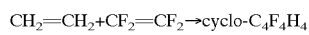

Reaction Scheme 3

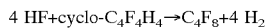

SUMMARY OF THE INVENTION

Therefore, an object of the present invention is to provide a simultaneous and selective preparation method of hexafluoropropylene and octafluorocyclobutane by stably carrying out a dimerization of TFE, by which solve the problems in the prior art including the difficulty in temperature control in case of carrying out a dimerization of TFE which is a severe exothermic reaction in a tubing reactor and the difficulty in operating a reactor caused by the problems in controlling reaction temperature, and the formation of carbon and solid polymer.

The above and other objects of the present invention, as embodied and broadly described herein, can be achieved by carrying out a dimerization of TFE in the presence of steam in a fluidized bed reactor system equipped with a nozzle for supplying steam.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention. In the drawings.

DETAILED DESCRIPTION OF THE PREFERRED EMBODIMENTS

Figure 1:
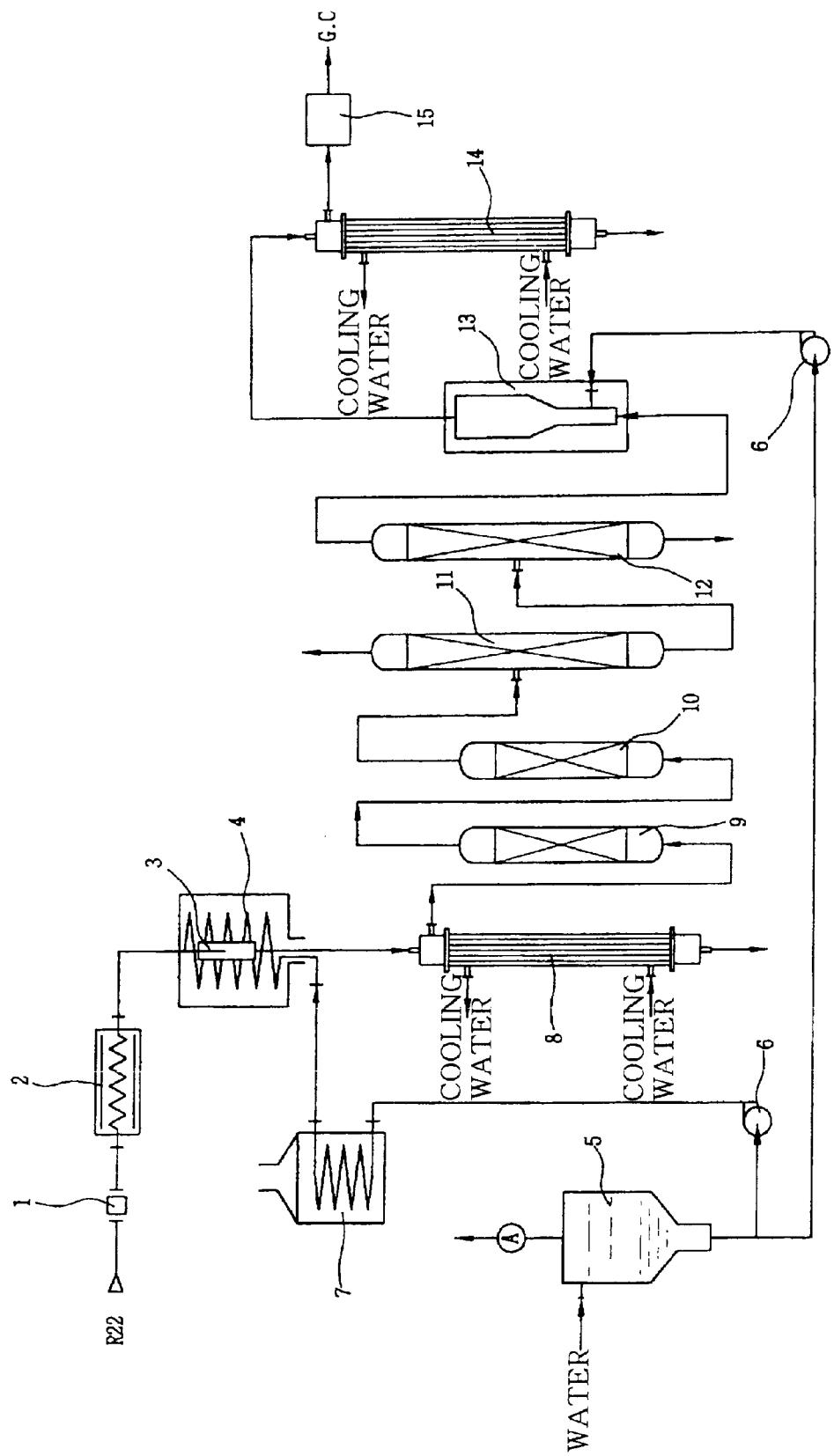
FIG. 1 is illustrating an apparatus for a thermal decomposition of R22 and dimerization of TFE in accordance with the present invention.

The present invention is characterized in that TFE, which is obtained through a thermal decomposition of R22, and steam are supplied into the fluidized bed reactor system equipped with a distributor for supplying steam, to perform dimerization of TFE, thereby simultaneously and selectively prepare hexafluoropropylene and octafluorocyclobutane.

In the present invention, the dimerization temperature can be controlled by adjusting an outer wall temperature of a reactor, a molar ratio between TFE and $H_2O$ supplied, and a contact time. In addition, the dimerization reaction is performed in a state that stream is supplied, so that not only the formations of carbon and polymer inside the reactor can be restrained but also a conversion of TFE and selectivities of HFP and RC318 can be controlled.

The present invention will be now described in detail. R22 is thermally decomposed with a pyrolyzer including a pre-heater, a super heating unit, a condenser and TFE distillation tower, to prepare TFE which is a starting material. The TFE is purified in the TFE distillation tower and then supplied into a bottom of the fluidized bed reactor. Water is supplied with a liquid pump and pre-heated, and then supplied into the flow of TFE in a state of steam through a distributor equipped at the bottom of the fluidized bed reactor.

In the present invention, a dimerization of TFE is performed while TFE and $H_2O$ with an appropriate molar ratio are supplied into the fluidized bed reactor, so that hexafluoropropylene and octafluorocyclobutane can be simultaneously and selectively produced. It is desirable that the molar ratio TFE/steam supplied into the fluidized bed reactor is 0.1–10.

The present invention can be represented by two-step reaction as shown in the following reaction schemes 5 and 6.

Reaction Scheme 5

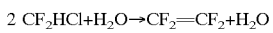

Reaction Scheme 6

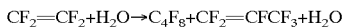

An apparatus for the thermal decomposition of R22 and dimerization of TFE used in the present invention is as shown in FIG. 1. The main parts of the apparatus in FIG. 1 are as follows:

1: Mass Flow controller
2. Pre-heater
3: Thermal Decomposition Reactor
4. Super Heating Unit
5. Water Tank
6. Pump
7. Steam Generator
8. HCl Absorber
9. NaOH Column
10. Dryer
11. Inert Distillation Tower
12. TFE Distillation Tower
13. Fluidized Bed Reactor
14. Acid Scrubber
15. Filter The present invention will be now described in more detail with reference to FIG. 1.

TFE is prepared by a thermal decomposition of R22 diluted with superheated steam according to the step as shown in reaction scheme 5. R22 is supplied into the pre-heater 2 with a mass flow controller 1. At this time, the temperature of the pre-heater is maintained in the range of 100–300° C. with a proportional-integral-derivative (PID) temperature controller. The pre-heated reactants are supplied into the thermal decomposition reactor 3 (reactor volume= 0.203 L).

Water for superheated steam is depressurized to remove oxygen under a vacuum in a water tank 5, equalized with nitrogen so as to be maintained at an atmospheric pressure, and is supplied in a certain amount into a steam generator 7 with a pump 6. The flow rate of a liquefied natural gas (LNG) is adjusted so that the temperature of steam at an outlet of the steam generator 7 can be maintained at a temperature of 500–600° C. The steam is superheated at 900–950° C. in a super heating unit 4 and then supplied into the thermal decomposition reactor 3.

When the reaction system is stabilized, R22, instead of nitrogen, is supplied in a desired flow rate, and then a thermal decomposition reaction is started. In order to restrain a side reaction, a gas at outlet of a reactor is quenched with an aqueous hydrochloric acid in a HCl absorber 8 made of graphite and rapidly cooled, and then HCl is removed with the absorber. The inside of the HCl absorber 8 is equipped with a rubber lining, and the absorbed heat of HCl and a sensitive heat are removed by circulating cooling water in the outside of a carbon.

The organic products which acid is removed in the HCl absorber is neutralized in a NaOH column 8 in order to remove a residual HCl, and then subjected to pass a dryer 10 filled with molecular sieve in order to remove moisture. Since low boiling materials are condensed at an upper part of the TFE distillation tower 12 and the concentration of TFE and oxygen increased, there is a high possibility to take place a room temperature polymerization. Therefore, in order to stabilize TFE, α-pinene (Wako Pure Chemical Co.) is supplied at a speed of 0.005 ml/min as a polymerization inhibitor.

An inert material such as $N_2$, tetrafluoromethane, R23 and hexafluoroethane in reaction products is removed in an inert distillation tower 11, and non-reacted R22 and low boiling materials are separated in a TFE distillation tower 12 and then a purified TFE is obtained from the middle stage of the distillation tower.

When purity of TFE is above 99.99% by a GC analysis, it is supplied into the fluidized bed reactor 13 (outer diameter=60.6 mm, inner diameter=52.7 cam, length/diameter of reaction region (L/D)=6) made of stainless steel (SUS 310) passing through a flow rate controller, and then the dimerization reaction is performed thereon. An activated carbon is used as a heat medium for the fluidization. A minimum fluidizing velocity ($U_{mf}$) is measured in the fluidized bed reactor made of quartz, which is resulted in $U_{mf}$=4.6 cm/sec. Pure water is then supplied into the fluidized bed reactor with a pump so that the molar ratio TFE/$H_2O$ can be maintained at a constant value.

The product TFE is passed through an acid scrubber 14 in order to remove acid and then passed through a filter 15 in order to remove a solid polymer. The product is then analyzed with a gas chromatograph (Series 550P, Gow-Mac Co.) equipped with a thermal conductivity detector and a Poraplot Q capillary column (⅛ in, 3 m, SUS). The reaction product is also identified with a GC/MS (HP 5890/5971, Hewlett Packard Co.) having a Poraplot Q capillary column.

A GC calibration for the binary component systems of TFE-RC318 and RC318-HFP is performed, and a conversion and selectivity of the product are calculated from analytical data of the gas chromatograph. A GC area % can be assumed as a GC mole % because the amount of side products is so little, and therefore the area ratio of the gas chromatograph can be converted into a molar ratio. The conversion of TFE in the thermal decomposition reaction and the selectivities of RC318 and HFP can be calculated with the following equations (1) and (2), and selectivities of other components can be calculated from a carbon balance equation.

Conversion of TFE=(mole number of reacted TFE/mole number of supplied TFE)×100 (1)

Selectivity of R318 =[(2×mole number of produced R318)/(mole number of reacted TFE)]×100 (2)

Selectivity of HFP=[(1.5×mole number of produced HFP)/(mole number of reacted TFE)]×100 (3)

As described above, a fluidized bed reaction and purification system can be designed in consideration of operation conditions such as an efficient purification of TFE from the reaction mixture, a prevention of polymerization, an inhibition of carbon formation and a stable temperature control. Therefore, an efficient process for simultaneously preparing HFP and RC318 is provided according to the present invention.

The outer wall temperature of the reactor is controlled with thermocouples of two heating regions attached to an outer wall of the reactor. An actual reaction temperature varies depending on a temperature of outer wall, a molar ratio between TFE and steam and a contact time. The reaction temperatures $t_1$, $t_2$, $t_3$, $t_4$ and $t_5$ are measured with five thermocouples installed inside the fluidized bed to reactor. $t_1$ and $t_2$ are temperatures at the section where the fluidization of the reactants takes place, $t_3$, $t_4$ and $t_5$ are temperatures at the section where is made adiabatic for inhibiting polymerization of TFE. The reaction temperature for the dimerization of TFE is maintained at 600–780° C. Though the dimerization of TFE is a severe exothermic reaction, by using the fluidized bed reaction system which steam is supplied, the temperature inside the reactor can be evenly controlled.

The fluidized bed reaction apparatus installed with a steam supplying nozzle used in the present invention makes it possible to restrain a local temperature increase in, for example, a severe exothermic reaction in which a reaction temperature control is difficult, a thermal decomposition reaction in which an acid such as a hydrofluoric acid, hydrochloric acid, sulfuric acid or nitric acid is produced as a side product, an oxidation reaction, and the like.

EXAMPLE

The present invention will be now explained in more detail with the Examples and Comparative Examples. It is to be understood that these examples are merely illustrative and not intended to limit the scope of the present invention thereto.

EXAMPLE 1

HFP and RC318 were prepared simultaneously in the TFE dimerization reaction apparatus equipped with a fluidized bed reactor as shown in FIG. 1.

R22 was supplied into a pre-heater at 44.2 mol/h with a mass flow controller, pre-heated to the temperature of 200° C. and then supplied into a reaction system. Oxygen-free water was supplied into a steam generator with a pump at 333 mol/h to generate steam of 550° C. and the generated steam was then supplied into a super heating unit. R22 was thermally decomposed while a outlet temperature of the reactor was maintained at 740° C., to give TFE. The produced TFE is purified in a distillation tower and then supplied into the fluidized bed reactor at 5 mol/h. Steam was supplied into the TFE flow inside the fluidized bed reactor at 3 mol/h. A thermal decomposition reaction was carried out under the conditions where a molar ratio TFE/$H_2O$ was 1.67, a contact time was 13.86 seconds at a room temperature under an atmospheric pressure and reaction temperatures are of $t_1$=605° C., $t_2$604° C. and $t_3$601° C.

The conversion of TFE was 63.34%, and the selectivities of hexafluoropropylene and octafluorocyclobutane were 5.0% and 89.35%, respectively.

EXAMPLE 2

A dimerization reaction of TFE was performed under the same conditions as in Example 1, except that the temperatures of the fluidized bed reactor were $t_1$=662° C., $t_2$=662° C. and $t_3$=623° C. The conversion of TFE was 78.45%, and selectivities of hexafluoropropylene and octafluorocyclobutane were 9.42% and 84.66%, respectively.

EXAMPLE 3

A dimerization reaction was performed under the same conditions as in Example 1, except that the temperatures of the fluidized bed reactor were $t_1$=747° C., $t_2$=747° C. and $t_3$=707° C. A conversion of TFE was 82.78%, and selectivities of hexafluoropropylene and octafluorocyclobutane were 39.07% and 38.27%, respectively.

EXAMPLE 4

TFE was prepared with the same method as in Example 1. The produced TFE was supplied into the fluidized bed reactor at 2.85 mol/h, and steam was supplied into the TFE flow in the fluidized bed reactor at 3 mol/h. A dimerization reaction was performed under the conditions where a molar ratio TFE/$H_2O$ was 0.95, a contact time was 18.96 seconds, temperatures were $t_1$=662° C., $t_2$=663° C. and $t_3$=639° C.

The conversion of TFE was 81.83%, and selectivities of hexafluoropropylene and octafluorocyclobutane were 24.39% and 66.82%, respectively.

EXAMPLE 5

A dimerization reaction was performed under the same conditions as in Example 4, except that the temperatures of the fluidized bed reactor were $t_1$=737° C., $t_2$=737° C. and $t_3$=713° C.

The conversion of TFE was 92.65%, and selectivities of hexafluoropropylene and octafluorocyclobutane were 41.81% and 40.51%, respectively.

EXAMPLE 6

TFE was prepared with the same method as in Example 1. The produced TFE was supplied into the fluidized bed reactor at 3 mol/h, and steam was supplied into the TFE flow in the fluidized bed reactor at 0.75 mol/h. A dimerization reaction was carried out under the conditions where a molar ratio TFE/$H_2O$ was 4.0, a contact time was 29.57 seconds, temperatures were $t_1$=646° C., $t_2$=645° C. and $t_3$=600° C.

The conversion of TFE was 85.67%, and selectivities of hexafluoropropylene and octafluorocyclobutane were 29.02% and 55.63%, respectively.

Below Table 1 shows supply rates of TFE and steam, the molar ratios between TFE and $H_2O$, contact times based on the reactor inlet, temperatures $t_1$, $t_2$ and $t_3$, conversion of TFE and selectivities of each product in TFE dimerization reactions according to Examples 1 to 6.

with five thermocouples. The distance between thermocouple was 30 cm, and $T_3$, $T_4$ and $T_5$ were horizontal direction temperature distributions of the region where the reaction took place in the tubular reactor.

TFE was purified in the distillation tower and supplied into the tubular or at 5 mol/h, and a dimerization reaction was carried out thereon under conditions where a reaction pressure was 1.5 kg/$cm^2$, the temperatures $T_3$, $T_4$ and $T_5$ were 454–517° C.

The conversion of TFE at an early stage of the reaction was 91.3%, and selectivities of hexafluoroehylene and octafluorocyclobutane were 7.56% and 92.05%, respectively. The temperatures $T_3$, $T_4$ and $T_5$ of the reaction region were measured at 30 cm intervals based on the reactor inlet.

However, since the local exothermic reaction region was moved according to the outer wall temperature of the reactor and contact time, it was impossible to measure the temperature of the middle part between the thermocouples, and accordingly, an accurate temperature could not be checked. In addition, as the reaction proceeds, the amount of solid polymer formed was increased, and TFE was carbonized due to the local exothermic reaction to give $CF_4$. The produced carbon was accumulated in the tubular reactor and the line, working as a cause of a pressure increase, resulting in that the exothermic react ion was more accelerated.

Comparative Example 2

A thermal decomposition reaction of TFE was performed under the same conditions as in Comparative Example 1, except that temperatures $T_3$, $T_4$ and $T_5$ were maintained at 533–581° C. A conversion was 96.0%, and selectivities of hexafluoropropylene and octafluorocyclobutane were 18% and 79.79%, respectively.

The same reactor operational problems as in Comparative Example 1 was observed. In addition, as the reaction tem-

TABLE 1

| | | Contact | Temperature (° C.)* | | | | Selectivity (%) | | |
|---|---|---|---|---|---|---|---|---|---|
| Examples | TFE/$H_2O$ | time | $t_1$ | $t_2$ | $t_3$ | Conversion | HFP | RC318 | Others** |
| 1 | 1.67 | 13.86 | 605 | 604 | 601 | 63.34 | 5.0 | 89.35 | 5.65 |
| 2 | 1.67 | 13.86 | 662 | 662 | 623 | 78.45 | 9.42 | 84.66 | 5.92 |
| 3 | 1.67 | 13.86 | 747 | 747 | 707 | 82.78 | 39.07 | 38.27 | 22.66 |
| 4 | 0.95 | 18.96 | 662 | 662 | 639 | 81.83 | 24.39 | 66.82 | 8.79 |
| 5 | 0.95 | 18.96 | 737 | 737 | 713 | 92.65 | 41.81 | 40.51 | 17.68 |
| 6 | 4.0 | 29.57 | 646 | 646 | 600 | 85.67 | 29.02 | 55.63 | 15.35 |

*$t_1$ and $t_2$ were temperatures in the reaction region of the fluidized bed reactor, and $t_3$ is a temperature of a adiabatic region
**Mixtures of $CF_2$ = CHF, $CHF_3$ and $CHF_3CF_3$

Comparative Example 1

In a system for a thermal decomposition and purification as shown in FIG. 1, dimerization of TFE was carried out in a tubular reactor (inner diameter=21 mm, outer diameter=24.5 mm, L=1200 mm) instead of a fluidized bed reactor. Horizontal temperature distributions from the inlet to outlet of the tubular reactor $T_1$, $T_2$, $T_3$, $T_4$ and $T_5$ were measured peratures went up higher than those of the Comparative Example 1, a local exothermic reaction took place more severely, exposing a big problem of a reactor temperature control.

Below Table 2 shows TFE supply rates, reaction pressures, temperatures $T_3$, $T_4$ and $T_5$, conversion of TFE and selectivities of each product in dimerization of TFE of Comparative Examples 1 and 2.

TABLE 2

| | | | TFE Dimerization reaction condition | | | | | | |
|---|---|---|---|---|---|---|---|---|---|
| Comp. | TFE flow rate | Reaction | Temperature* | | | Conversion | Selectivity (%) | | |
| Examples | (mol/h) | pressure | T3 | T4 | T5 | (%) | R23 | HFP | RC318 | Others** |
| 1 | 5.0 | 1.5 | 496.4 | 517.4 | 454.3 | 91.3 | 0.24 | 7.56 | 92.05 | 0.15 |
| 2 | 5.0 | 1.5 | 581.3 | 538.2 | 533.2 | 96.0 | 0.23 | 18.0 | 79.79 | 1.98 |

$T_3$, $T_4$ and $T_5$ were horizontal direction temperature distributions from the middle portion to the outlet of the tubular reactor.
**Mixtures of $CF_2 = CHF$ and $CHF_3CF_3$

Comparative Example 3

In the apparatus for thermal decomposition reaction as shown in FIG. 1, a thermal decomposition reaction of R22 was performed with a super heated steam to prepare HFP and RC318 simultaneously. R22 was supplied into the pre-heater at 44.2 mol/h with a mass flow controller, pre-heated at 200° C. and then supplied into a super heating unit (reactor volume=0.203 L). Oxygen-free water was supplied into the steam generator at 333 mol/h with a pump to generate steam of 550° C. and then supplied the steam into the super heating unit.

A thermal decomposition reaction of R22 was performed at 739° C. to prepare HFP and RC318. A conversion of R22 was 70.47%, and selectivities of tetrafluoroethylene, hexafluoropropylene and octafluorocyclobutane were 98.78%, 0.09% and 0.37%, respectively.

Comparative Example 4

A thermal decomposition reaction of R22 was performed under the same conditions as in Comparative Example 3, except that water was supplied into the steam generator at 278 mol/h and the thermal decomposition reactor was maintained at a temperature of 718° C.

A conversion of TFE was 81.86%, and selectivities of tetrafluoroethylene, hexafluoropropylene and octafluorocyclobutane were 93.93%, 3.83% and 1.0%, respectively.

Since TFE is a main product, and small amounts of HFP and RC318 were produced, this process is not suitable for simultaneously preparing HFP and RC318.

Below Table 3 shows supply rates of R22 and steam, reaction temperatures, conversion of R22 and selectivities of each product in thermal decomposition reactions of R22 of the Comparative Examples 3 and 4.

In comparison of results in Examples and Comparative Examples, it is noted that due to the local severe exothermic reaction, the conversion of TFE in the tubular reactor were higher than those in the fluidized bed reactor. In addition, at the initial stage of the reaction, selectivities of RC318 were higher in the tubular reactor than in the fluidized bed reactor. However, in the reactions in the tubular reactor, as the reaction proceeded, local exothermic reaction regions were moved, and therefore, the temperature went up and the selectivities of RC318 were reduced while the selectivities of HFP were increased along with increasing the formation of carbon.

As so far described, according to the method for simultaneously and selectively preparing hexafluoropropylene and octafluorocyclobutane of the present invention, the reactor operational problems due to the formation of carbon and solid polymer inside the tubular reactor, resulted from the severe exothermic reaction of TFE were highly improved. In addition, the dimerization temperature of TFE was easily controlled by adjusting the outer wall temperature of the reactor, the molar ratio $TFE/H_2O$ and the contact time. Moreover, by supplying stream, formation of the solid polymer and carbon was inhibited, and the selectivities of HFP and RC318 as well as the conversion of TFE can be evenly controlled.

What is claimed is:

1. A method of simultaneous and selective preparation of hexafluoropropylene and octafluorocyclobutane comprising the steps of:
    (a) thermally decomposing difluorochloromethane to obtain tetrafluoroethylene and then supplying the resulting tetrafluoroethylene into a fluidized bed reactor equipped with a distributor for supplying steam; and
    (b) supplying steam into a flow of tetrafluoroethylene supplied into the fluidized bed reactor, through a dis-

TABLE 3

| | Thermal decomposition reaction conditions of R22 in the presence of super heated steam | | | | | | | |
|---|---|---|---|---|---|---|---|---|
| Comp. | Flow rate of R22 | Stream flow rate | Reaction Temperature | Conversion | Selectivity (%) | | | |
| Examples | (mol/H) | (mol/H) | (° C.)* | (%) | TFE | HFP | RC318 | Others** |
| 3 | 0.044 | 0.333 | 739 | 70.47 | 98.78 | 0.09 | 0.375 | 0.76 |
| 4 | 0.044 | 0.276 | 718 | 81.86 | 93.93 | 3.83 | 1.0 | 1.24 |

*Temperature were based on a temperatures of the reactor outlet
**Mixtures of $CF_2 = CHF$ and $CF_2CFCl$ tributor for supplying steam at a molar ratio of 0.1–10 of tetrafluoroethylene/stream, and then performing dimerization of tetrafluoroethylene in the fluidized bed reactor.

2. The method according to claim 1, wherein the step (a) comprises:

i) thermally decomposing difluorochloromethane in a thermal decomposition apparatus including a preheater, a super heating unit, a condenser and a distillation tower to obtain tetrafluoroethylene;

ii) passing the produced tetrafluoroethylene sequentially through a HCl absorber, NaOH column and dryer;

iii) purifying the tetrafluoroethylene in the distillation tower; and iv) supplying the purified tetrafluoroethylene into the fluidized bed reactor from the middle stage of the distillation tower.

3. The method according to claim 1, wherein the steam in step (b) is generated by supplying water with a liquid pump and converting the water into steam with pre-heating, and then supplied into the tetrafluoroethylene flow through a the distributor equipped at a bottom of the fluidized bed reactor.

4. The method according to claim 1, wherein a temperature of the dimerization of tetrafluoroethylene in step (b) is maintained in the range of 600–780° C.

5. The method according to claim 1, wherein a contact time of reactants in the fluidized bed reactor is maintained for 1–35 seconds.

* * * * *